United States Patent [19]

Downey

[11] Patent Number: 4,813,433

[45] Date of Patent: Mar. 21, 1989

[54] SYRINGE FOR WITHDRAWING BLOOD

[76] Inventor: John M. Downey, 11317 College View Dr., Silver Spring, Md. 20902

[21] Appl. No.: 180,007

[22] Filed: Apr. 11, 1988

[51] Int. Cl.$^4$ .............................................. A61B 5/14
[52] U.S. Cl. .................................... 128/765; 128/766; 604/231
[58] Field of Search ..................... 128/760, 762-766, 128/771; 604/38, 201, 205, 231-235, 239

[56] References Cited

U.S. PATENT DOCUMENTS 1,704,678  3/1929  Brown .............................. 604/234 X
4,257,426  3/1981  Bailey ............................... 128/765 X Primary Examiner—Edward M. Coven
Assistant Examiner—Angela D. Sykes
Attorney, Agent, or Firm—John S. Roberts, Jr.

[57] ABSTRACT

A syringe for withdrawing fluids which consists of novel new one-handed operated syringe. Said one-handed or therapeutic syringe is described as a therapeutic syringe comprising a double compartmented housing, a piston disposed in one of said compartments, a piston rod connected to said piston controlling the movement of said piston in a barrel, vent means associated with said piston compartment, said other non-piston compartment being formed with needle hub for supporting a needle and having an opening in fluid communication with said piston compartment whereby when said piston is moved forward in said barrel in said piston compartment, air will be discharged therefrom while drawing liquid into said other compartment.

8 Claims, 1 Drawing Sheet

SYRINGE FOR WITHDRAWING BLOOD

BACKGROUND OF THE INVENTION

The prior art is aware of the typical handheld syringe which is used by the general population for withdrawing blood and the like for sampling purposes. Generally, these syringes include a cylinder, a piston disposed therein, a piston rod secured to said piston and extending outwardly of one end of said cylinder and terminating in a handle for controlling movement of the same, and a hollow needle extending from the other. In use, the needle point is introduced into the body from which the fluid sample is to be withdrawn and held thereat by grasping the cylinder with one hand and simultaneously pulling on the handle means with the other hand to control a vacuum to withdraw the fluid from the body through the hollow needle into the cylinder. Thereafter the fluid sample is used, or processed, in the normal fashion.

It is apparent then that the major drawback associated with conventional syringes is the fact that it is a two-handed process which increases the pain, increases the chance of needle trauma to the vessel wall, increases the chance of accidental puncturing of the vein with its associated bleeding and the inflammation of the vein.

It is the object of the present invention to provide a new one-handed operated syringe which will obviate the deficiencies of the conventional syringe enumerated hereinabove. In a search of the prior art in the U.S. Patent Office, Russian Pat. No. 445,411 discloses a syringe of the same general type as applicants.

SUMMARY OF THE INVENTION

The syringe of the present invention is one that is designed to be manipulated by one hand, thereby freeing the other hand to stabilize the skin, localize the site and to palpate the progress of the procedure. The present syringe accomplishes all of the described advantages in a rather simple manner by designing the plunger to move forward in a partitioned cyliner to produce a vacuum thereby causing the fluid to be drawn into the other part thereof. The syringe comprises a cylinder housing, a partition wall dividing the interior into two compartments, a seal closing one end of the cylinder and an end wall closing the other end thereof, a wall engaging piston disposed in one of the compartments having a piston rod extending therefrom outwardly of an opening provided in the seal, with a handle means provided on the free end thereof, a needle hub provided in the end wall communicating with the other compartment, and a vent opening provided in the partition wall adjacent the seal. Prior to use, the needle is secured to the needle hub and the piston is disposed proximal to the seal end of the cylinder housing, the user than grasps the syringe in one hand and injects the needle into the body from which the sample is to be withdrawn, and thereafter pushes the handle means causing the piston to move forwardly thereby causing a vacuum to its rear causing the fluid to enter the other compartment. After filling, the sample is then handled in a conventional manner.

DESCRIPTION OF THE PREFERRED EMBODIMENT

Figure 1:
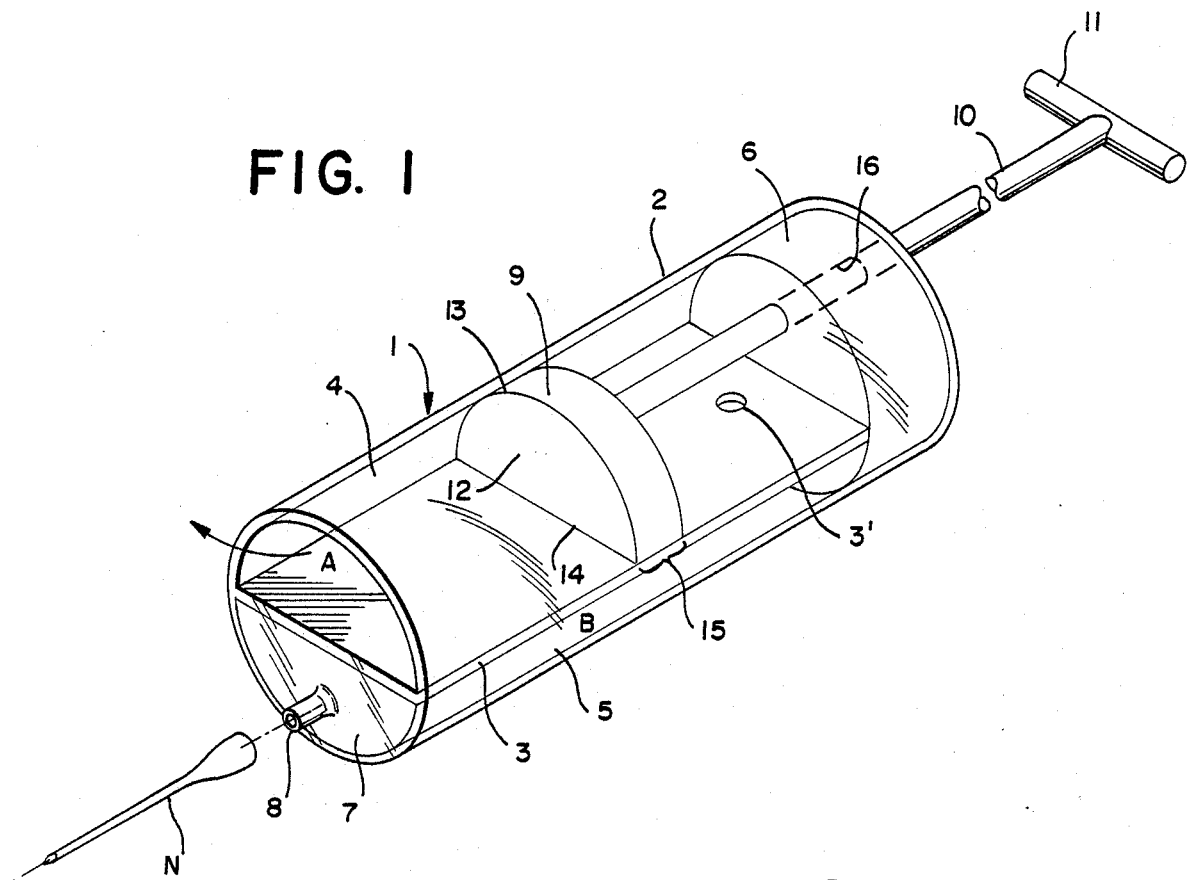
FIG. 1 is a perspective view of the syringe.

With reference to FIG. 1, the syringe of the present invention is identified generally by the numeral 1 and is seen to be comprised of a housing 2, a partition 3, dividing the housing into two compartments 4,5, seal means 6, closing one end of the housing 2, a partial end wall 7 closing the compartment 5, a needle hub 8 formed in the end wall 7, a piston 9 disposed in the other compartment 3, a piston rod 10 connected to said piston 9 and extending through an opening in said seal means 6 outwardly of said housing 2 and terminating in a handle 11.

With continuing reference to FIG. 1, the housing 2 is seen to be cylindrical in shape and is preferably made from transparent glass, plastic or the like and is divided into at least two compartments 4,5 by the partition wall 3, partial end wall 7 and the seal means 6. It is important that the partition wall 3 either be made integral with the main housing 2 or if added as a separate component be such that it be generally airtight except for the provision of an opening 3' adjacent the seal 6. A hollow needle hub 8 is formed and extends outwardly of the partial end wall 7 and communicates with the interior of compartment 5. As seen, the piston 9 is disposed in compartment 4 and is of a generally semi-circular shape 12 with the arcuate portion 13 in close frictional sliding contact with the interior wall of housing 2 while the flat portion 14 is in close frictional sliding contact with the partition wall 3.

The piston 9 is made from any material which will provide an airtight relationship with the interior of the housing 2 when the same is moved therein. The thickness 15 of the piston is also dependent on the material selected to fabricate the piston to attain the airtight relationship. The piston rod 10 is secured to the piston 9 and passes through an opening 16 in the seal 6 outwardly of the housing 2 and terminates in the control handle 11 for manipulating and controlling the piston 9.

The seal means 6, like the piston 9 is also selected from material to make the housing 2 airtight. The opening 16 in the seal 6 is in tight, frictional, sliding relationship with the rod 10 to maintain the airtight relationship in the housing 2.

With continuing reference to FIG. 1, it is seen that the end of compartment 4 opposite the seal means 6 is wall-less for a reason to be explained hereinafter.

To use the syringe 1 of the present invention, the operator places a hollow needle N on the hub 8 and places the syringe in one hand and with the other hand uses the same to stabilize the skin and localize the site for placing the needle. The needle N is then forced into and through the skin by the one hand, and after doing so, he places his thumb on the handle 11 and pushes it inwardly causing the piston 9 to move forwardly in the housing 2 which simultaneously forces the air in front of the piston out through the wall-less opening in the compartment 4 and causes a vacuum in the other compartment 5 by drawing air therefrom through the opening 3'. As this transpires, fluid is drawn through the hollow needle N, the needle hub 8 and into the compartment 5. After the sample is withdrawn and the needle N removed from the housing, the same can be processed in the normal fashion.

Figure 2:
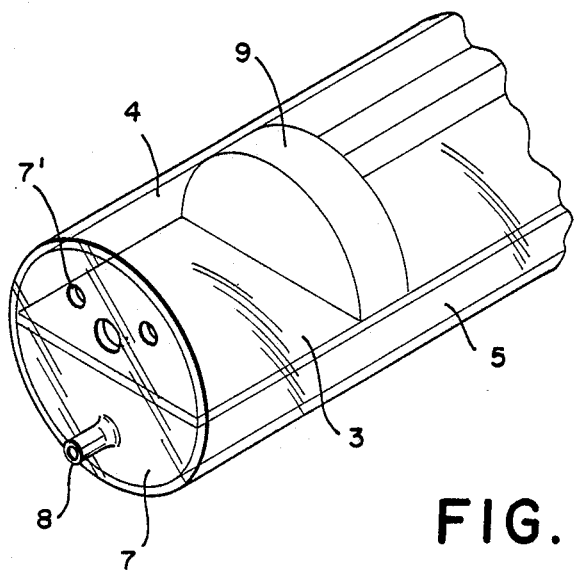
FIG. 2 shows a modification of the end wall of the syringe

While I have illustrated and described a preferred embodiment, it is to be understood that I do not limit myself to the precise construction of the syringe. For example, and as seen in FIG. 2, the partial end wall 7 can be extended to cover both compartments with the wall portion enclosing the compartment 4 be provided with openings 7' through which the air can be forced.

Having thus described my invention, what I claim as new and desire to secure by U.S. Letters Patent is:

1. A syringe comprising an elongated housing, said housing having an open end and a substantially closed second end, seal means closing said open end, partition means dividing the interior of the housing into at least two separate compartments, piston means disposed in one of said compartments, a piston rod extending from said piston means through said seal means outwardly of said compartment, an end wall closing the other compartment, at least one opening disposed in said end wall and terminating in a needle hub, and a further opening disposed in said partition means adjacent to said seal means whereby when the piston rod and piston means are pushed forwardly, air will be expelled from said piston compartment while creating a vacuum in said second chamber thereby causing fluid to be drawn therein.

2. The syringe of claim 1 wherein the housing is circular in cross section.

3. The syringe of claim 2 wherein the piston is of semi-circular shape with the flat portion thereof engaging the partition means and the semi-circular portion engaging the circular configuration of the housing.

4. The syringe of claim 3 wherein a needle is disposed in said hub.

5. The syringe of claim 4 wherein handle means are disposed on a free end of said piston rod to facilitate movement of the same.

6. The syringe of claim 5 wherein the housing is made from transparent material.

7. A therapeutic syringe comprising a double compartmented housing, a piston disposed in one of said compartments, a piston rod connected to said piston controlling the movement of said piston in a barrel, vent means associated with said piston compartment, said other non-piston compartment being formed with needle hub for supporting a needle and having an opening in fluid communication with said piston compartment whereby when said piston is moved forward in said barrel in said piston compartment, air will be discharged therefrom while drawing liquid into said other compartment.

8. The syringe of claim 7 wherein the movement of said piston controls the amount of vacuum in said other compartment.

* * * * *